United States Patent

Chess

(10) Patent No.: US 10,092,855 B2
(45) Date of Patent: Oct. 9, 2018

(54) $CO_2$ EXTRACTION AND FILTRATION SYSTEM

(71) Applicant: Fritz Chess, Seattle, WA (US)

(72) Inventor: Fritz Chess, Seattle, WA (US)

(*) Notice: Subject to any disclaimer, the term of this patent is extended or adjusted under 35 U.S.C. 154(b) by 0 days.

(21) Appl. No.: 15/212,342

(22) Filed: Jul. 18, 2016

(65) Prior Publication Data

US 2017/0014731 A1     Jan. 19, 2017

Related U.S. Application Data

(60) Provisional application No. 62/315,410, filed on Mar. 30, 2016, provisional application No. 62/193,118, filed on Jul. 16, 2015.

(51) Int. Cl.
*B01D 11/02* (2006.01)
*B01D 61/24* (2006.01)
*B01D 61/32* (2006.01)
*C12C 3/00* (2006.01)
(Continued)

(52) U.S. Cl.
CPC ........ *B01D 11/0203* (2013.01); *B01D 61/246* (2013.01); *B01D 61/32* (2013.01); *C07C 7/00* (2013.01); *C11B 1/104* (2013.01); *C12C 3/00* (2013.01); *B01D 2311/14* (2013.01);
(Continued)

(58) Field of Classification Search
CPC .................................................. B01D 11/0203
See application file for complete search history.

(56) References Cited

U.S. PATENT DOCUMENTS 3,349,919 A * 10/1967 Royer .................... B01D 29/58
                                                                    210/232
4,466,923 A     8/1984 Friedrich
(Continued)

FOREIGN PATENT DOCUMENTS

EP       1536810      8/2012
WO     02064109    8/2002

OTHER PUBLICATIONS

Sarmento et al. "Use of Reverse Osmosis Membranes for the Separation of Lemongrass Essential Oil and Supercritical CO2". Brazillian Journal of Chemical Engineering. vol. 21, No. 02, pp. 285-291, Apr.-Jun. 2004.*

*Primary Examiner* — Donald R Spamer
(74) *Attorney, Agent, or Firm* — Emerson, Thomson, Bennett, LLC; Roger D. Emerson

(57) ABSTRACT

Provided is an extraction system which can be used to recover light oils and other organic materials during a supercritical or subcritical fluid extraction. The extraction system may include a dual purpose pressure vessel which can be used as an independent, full spectrum extractor by adding organic material within a compartment within the vessel and passing liquefied, compressed gases onto and through organic material as well as a separator to separate the extracting fluid from the extracted material. Filter membranes having different size pore openings designed to capture and retain various compounds based on their molecular size may be used in conjunction with the pressure vessel. The filter membranes are part of a filtration system which may be incorporated as an internal component of the pressure vessel or may be utilized at different locations within the extraction system.

7 Claims, 6 Drawing Sheets

(51) Int. Cl.
*C11B 1/10* (2006.01)
*C07C 7/00* (2006.01)

(52) U.S. Cl.
CPC ...... *B01D 2317/02* (2013.01); *B01D 2317/08* (2013.01); *Y02P 20/544* (2015.11)

(56) References Cited

U.S. PATENT DOCUMENTS

| | | | | |
|---|---|---|---|---|
| 4,554,163 | A * | 11/1985 | Weber | B01D 11/0203 424/725 |
| 5,398,806 | A | 3/1995 | Quinn | |
| 5,637,209 | A | 6/1997 | Wright et al. | |
| 5,961,835 | A * | 10/1999 | Sarrade | B01D 11/0203 210/634 |
| 7,001,620 | B2 | 2/2006 | Gow et al. | |
| 7,025,992 | B2 | 4/2006 | Whittle et al. | |
| 7,344,736 | B2 | 3/2008 | Whittle et al. | |
| 8,895,078 | B2 | 11/2014 | Mueller | |
| 2004/0049059 | A1 | 3/2004 | Mueller | |
| 2004/0159337 | A1* | 8/2004 | Johnson | A47L 15/4204 134/18 |
| 2006/0251742 | A1 | 11/2006 | Gow et al. | |
| 2007/0254063 | A1* | 11/2007 | Aerts | C12C 3/08 426/11 |
| 2008/0148953 | A1* | 6/2008 | Maldanis | A47J 31/0576 99/279 |
| 2011/0133120 | A1* | 6/2011 | McGhee | B01D 11/0219 252/182.12 |
| 2013/0144099 | A1* | 6/2013 | Tasaka | C10G 67/00 585/314 |
| 2014/0248379 | A1 | 9/2014 | Mueller | |

* cited by examiner

CO₂ EXTRACTION AND FILTRATION SYSTEM

I. BACKGROUND

A. Technical Field

Provided is a carbon dioxide extraction apparatus for subcritical and supercritical extractions which may optionally use filter membranes for isolating compounds during carbon dioxide extraction.

B. Description of Related Art

Supercritical $CO_2$ extraction was originally developed by Germany in the 1930's to extract oil from shale for the war effort of World War II. After the conflict ended, it was shown that the same process could be used for extracting flavoring oils from hops for the German beer industry. To this day, the largest $CO_2$ extractors are used for making hops oils for beer.

$CO_2$ extraction generally operates in the following manner. First, plant or other organic or raw materials are inserted into a vessel which operates as an extractor. Next, $CO_2$ gas is pumped from a $CO_2$ tank through a conduit to the extractor. The extractor is pressurized and maintained at a certain temperature so that $CO_2$ gas is compressed to a liquid or supercritical fluid upon its entry into the extractor. In certain cases, the exterior of the extractor may be insulated with an insulation jacket to assist in maintaining the temperature within the extractor. As the liquefied $CO_2$ passes through the plant or other organic or raw material within the extractor, it acts as a solvent, removing (i.e., extracting) various oils and compounds from the plant or other raw materials. The liquefied $CO_2$ containing the extracted oils and compounds is then transferred or pumped to a separator. The separator is maintained at a different temperature and pressure than the extractor which results in the separation of the oil and other extracted compounds from the liquefied $CO_2$ and the conversion of liquefied $CO_2$ into $CO_2$ gas. For example, in certain cases, the extractor is maintained at a pressure of about 1000 psi and the separator is maintained at a pressure of about 200 to about 400 psi to enable the extraction process to be carried out. After entering the separator, oil and other extracted compounds separate from the liquefied $CO_2$ and fall into a collection vessel at the bottom of the separator while the $CO_2$ gas is transferred or pumped through a conduit to either the $CO_2$ tank or to the extractor to be recirculated through the system.

The advantages of $CO_2$ extraction include its ability to be tuned for different extraction parameters by adjusting temperature and pressure and the fact that it leaves no toxic solvent residues within the final product. The disadvantages of $CO_2$ extraction are that it is a complicated process which involves a lot of technical hurdles including the pumping of fluids and achieving and maintaining the specific pressure and temperature swings of fluids and materials involved in the process. Another drawback of $CO_2$ extraction has been the fact that a lot of the monoterpenes or flavor and fragrance oils are lost in the process because they remain volatile and stay entrained in the $CO_2$ vapor rather than falling out into the separators during extraction. These issues have been resolved by Applicant by the development of a method for $CO_2$ extraction which involves no pump and wherein the entire process may be completed within one vessel. This drastically reduces the complexity, costs, and technical problems that $CO_2$ extraction has always been known for. To accomplish the extraction process within a single vessel, a reflux distiller can be incorporated into the system between the separator and the condensing system to cool the $CO_2$ vapor coming from the separator enough to drop out the light oils but not enough to liquefy the $CO_2$.

Moreover, despite the fact that the technology for $CO_2$ extraction has a wide range of applications, an additional obstacle exists in that its use has been limited in use due to the high price of manufacturing the various equipment including the vessels, valves, pumps, etc. required to carry out the extraction process. The source of the expense for the extraction equipment lies in the fact that such equipment must be manufactured in accordance with rigorous standards to meet the operational conditions of the extraction process such as extreme operational pressures (e.g., up to about 15,000 psi). The other source of high operational costs are associated with the energy used to perform an extraction. The first energy intensive part of the process involves a high pressure pump which must first compress the $CO_2$ to anywhere from 800 to 15,000 psi through the extractor vessel. The resulting stream of extract saturated $CO_2$ then de-pressurizes into a separator vessel in which the $CO_2$ flashes to vapor thereby causing the extract to drop out into the bottom of the vessel. The vaporized $CO_2$ must then be cooled so it returns to a liquid state before it returns to the pump inlet. These steps of pumping, compressing, depressurizing and cooling are all very energy intensive.

Moreover, $CO_2$ acts as a refrigerant when it de-pressurizes causing extreme cooling well below 0° F. To counteract this effect, the separators must be heated in order to compensate for the cooling effect. Typically, separators must be kept at 50-60° C. to function efficiently.

Pressurizing the $CO_2$, heating it as it cools, then cooling it when it is hot requires very high electricity usage. In certain embodiments, the present disclosure eliminates several of the pressure vessels involved in separation of extracts from $CO_2$ and condensing $CO_2$. It also eliminates the associated heaters and chillers in such embodiments. Pumping costs will be reduced because the circulating $CO_2$ will remain at one steady pressure at the inlet and outlet of the pump allowing it to work less hard. Manufacturing and operational costs will be dramatically lower thereby making the technology more affordable for industry.

II. SUMMARY

The present disclosure relates to a process, apparatus and system for continuously circulating pressurized subcritical or supercritical $CO_2$ through a solid matrix for extracting desired compounds from the matrix. The extraction system incorporates a method of using a high pressure pump to direct liquefied carbon dioxide to an extraction vessel filled with ground up solid material. $CO_2$ can be heated to a supercritical state or cooled to subcritical state prior to entering the extractor vessel. After passing through the material to be extracted within the extraction vessel, dissolved constituents may pass through a series of membrane filters. The filter or filters within the first series generally have the largest pore size and catch the largest molecules which are generally waxes and/or chlorophyll. The filter or filters within the second series will generally have smaller diameter pores to capture a generally a translucent, syrup like consistency which contains the desired compounds. The filter or filters within the third series will generally have the smallest or tightest pore size. These filters are designed to capture monoterpenes which are very small molecules which compose the majority of tastes and fragrances. The extraction system may also include a dual purpose apparatus referred to as an extractor-separator pressure vessel which combines the extraction and separation of constituents within a single pressurized vessel.

Provided is an extraction system. The extraction system includes: a tank containing $CO_2$ gas which comprises an inlet for filling the tank with $CO_2$ gas and an outlet for allowing the gas to enter the extraction system; an extraction vessel comprising an inlet which receives $CO_2$ gas through one or more conduits and an outlet, wherein the extraction vessel is pressurized and maintained at a temperature to convert the carbon dioxide gas to liquefied carbon dioxide, further wherein the liquefied $CO_2$ is passed through organic material placed within the extraction vessel to extract various compounds from the organic material; optionally, a first separator comprising an inlet and an outlet wherein the first separator receives liquefied $CO_2$ from the extraction vessel through one or more conduits which connect the outlet of the extraction vessel to the inlet of the first separator, further wherein the first separator is maintained at a different temperature and pressure than the extraction vessel to convert the liquefied $CO_2$ into $CO_2$ gas, separates compounds extracted from the organic material from the liquefied $CO_2$ and includes a collection zone for collecting compounds separated from the liquefied $CO_2$; optionally, a second separator in combination with a first separator comprising an inlet and an outlet wherein the second separator receives at least one of: 1) overflow liquid $CO_2$ from the first separator through one or more conduits which connect the outlet of the first separator with the inlet of the second separator and 2) liquefied $CO_2$ from the extraction vessel through one or more conduits which connect the outlet of the extraction vessel to the inlet of the second separator, further wherein the second separator is maintained at a different temperature and pressure than the extraction vessel to convert the liquefied $CO_2$ into $CO_2$ gas, separates compounds extracted from the organic material from the liquefied $CO_2$ and includes a collection zone for collecting compounds separated from the liquefied $CO_2$; an accumulator comprising an inlet and an outlet, wherein the inlet of the accumulator is connected to the outlet of the extractor-separator pressure vessel through one or more conduits for receiving $CO_2$ from the outlet of the extractor-separator pressure vessel; and a filtration system which is integrated within the extraction system in at least one of the following arrangements: 1) within the extraction vessel; 2) outside of the extraction vessel; 3) outside of the extraction vessel and between the extraction vessel and the first separator; 4) within the first separator; 5) within the second separator; 6) outside of the first separator and the second separator and between the first separator and the second separator; and 7) outside of and downstream from the first separator and the second separator. In certain embodiments, the filtration system is incorporated outside of the extraction vessel for filtering liquefied $CO_2$ containing extracted material and the extraction system does not include one or more separator vessels.

Also provided is an extraction system which includes the following components: a tank containing $CO_2$ gas which comprises an inlet for filling the tank with $CO_2$ gas and an outlet for allowing the gas to enter the extraction system; optionally, an extraction vessel comprising an inlet which receives $CO_2$ gas through one or more conduits and an outlet, wherein the extraction vessel is pressurized and maintained at a temperature to convert the carbon dioxide gas to liquefied carbon dioxide, further wherein the liquefied $CO_2$ is passed through organic material placed within the extraction vessel to extract various compounds from the organic material; optionally, at least one separator in combination with the extraction vessel comprising an inlet and an outlet wherein the first separator receives liquefied $CO_2$ from the extraction vessel through one or more conduits which connect the outlet of the extraction vessel to the inlet of the first separator, further wherein the first separator is maintained at a different temperature and pressure than the extraction vessel to convert the liquefied $CO_2$ into $CO_2$ gas, separates compounds extracted from the organic material from the liquefied $CO_2$ and includes a collection zone for collecting compounds separated from the liquefied $CO_2$; an extractor-separator pressure vessel comprising an inlet and an outlet wherein the extractor-separator pressure vessel receives $CO_2$ gas from at least one of: 1) the $CO_2$ tank through one or more conduits which connect the $CO_2$ tank with the inlet of the extractor-separator pressure vessel; 2) overflow liquid $CO_2$ from the separator through one or more conduits which connect the outlet of the separator with the inlet of the extractor-separator pressure vessel and 3) liquefied $CO_2$ from the extraction vessel through one or more conduits which connect the outlet of the extraction vessel to the inlet of the extractor-separator pressure vessel, wherein the extractor-separator pressure vessel includes an extraction chamber for housing organic material to be extracted, a condenser zone located at the top portion of the extractor-separator pressure vessel, a collection zone located at the bottom portion of the second separator and a main body located between the condenser zone and the collection zone, wherein $CO_2$ vapor enters the top portion of the extractor-separator pressure vessel and is liquefied to a supercritical fluid, wherein the liquefied $CO_2$ is passed through the organic material housed within the extraction chamber to extract various compounds and is subsequently delivered to the collection zone, wherein the collection zone is maintained at a temperature and a pressure which allows the liquefied $CO_2$ to vaporize, wherein the vaporized $CO_2$ rises within a main body portion of the second separator to separate itself from compounds entrained within the liquefied $CO_2$, wherein the vaporized $CO_2$ enters the condenser zone of the extractor-separator pressure vessel and contacts a condenser maintained at the top portion of the extractor-separator pressure vessel, wherein any organic compounds remaining within the $CO_2$ vapor condenses out on the condenser and drips to the extraction chamber to further extract compounds from the organic material and subsequently enters the collection zone at the bottom portion of the extractor-separator pressure vessel for collection; and an accumulator comprising an inlet and an outlet, wherein the accumulator receives $CO_2$ from the extractor-separator pressure vessel through one or more conduits. According to another aspect of the present disclosure, extraction system may include a filtration system which is integrated within the extraction system in at least one of the following arrangements—1) within the extraction vessel; 2) outside of the extraction vessel; 3) outside of the extraction vessel and between the extraction vessel and a first separator; 4) within the first separator; 5) within a second separator; 6) outside of the first separator and the second separator and between the first separator and the second separator; 7) outside of and downstream from the first separator and the second separator and outside of and upstream from the extractor-separator pressure vessel; 8) within the extractor-separator pressure vessel; and 9) between the extractor-separator pressure vessel and the accumulator.

According to another aspect of the present disclosure, the filtration system is integrated within the extractor-separator pressure vessel.

According to another aspect of the present disclosure, the extraction system includes a second external condenser positioned between the extractor-separator pressure vessel and the accumulator, wherein the second external condenser includes an inlet for receiving vaporized $CO_2$ through a conduit connected to the outlet of the extractor-separator pressure vessel, condenses the vaporized $CO_2$ to liquid $CO_2$ and an outlet for transferring liquid $CO_2$ to the accumulator through a conduit which connects the outlet of the second external condenser with the inlet of the accumulator.

According to another aspect of the present disclosure, the filtration system is positioned below the extraction chamber, further wherein the filtration system comprises a first series of filtration chambers, a second series of filtration chambers and a third series of filtration chambers, wherein each series of filtration chambers comprises a first chamber and a second chamber and a flow control/pressure relief valve to control the flow of liquid $CO_2$ between the first chamber and the second chamber within each series of filtration chambers, wherein each chamber houses a high pressure filter membrane and a pressure gauge positioned before and after the filter membrane within each chamber to indicate how much extract is filled within the chamber housing the filter membrane, wherein the extractor-separator pressure vessel further comprises at least one conduit allowing the liquefied $CO_2$ exiting the filtration system to be recirculated through the extraction chamber after the liquefied $CO_2$ passes through at least one filtration chamber, wherein the high pressure filter membrane within the first series of chambers has a pore size greater than the high pressure filter membrane within the second series of chambers and wherein the high pressure filter membrane within the second series of chambers has a pore size greater than the high pressure filter membrane within the third series of chambers.

According to another aspect of the present disclosure, the filtration system is integrated between the second external condenser and the accumulator, further wherein the filtration system comprises a first series of filtration chambers, a second series of filtration chambers and a third series of filtration chambers, wherein each series of filtration chambers comprises a first chamber and a second chamber and a flow control/pressure relief valve to control the flow of liquid $CO_2$ between the first chamber and the second chamber within each series of filtration chambers, wherein each chamber houses a high pressure filter membrane and a pressure gauge positioned before and after the filter membrane within each chamber to indicate how much extract is filled within the chamber housing the filter membrane, wherein the filtration system further comprises at least one conduit connecting at least one outlet within the filtration to at least one inlet within the extractor-separator pressure vessel allowing the liquefied $CO_2$ exiting the filtration system to be recirculated through the extractor-separator pressure vessel after the liquefied $CO_2$ passes through at least one filtration chamber, wherein the high pressure filter membrane within the first series of chambers has a pore size greater than the high pressure filter membrane within the second series of chambers and wherein the high pressure filter membrane within the second series of chambers has a pore size greater than the high pressure filter membrane within the third series of chambers.

Also provided is an extraction system which includes the following components: a tank containing $CO_2$ gas which comprises an inlet for filling the tank with $CO_2$ gas and an outlet for allowing the gas to enter the extraction system; an extractor-separator vessel comprising an inlet and an outlet wherein the extractor-separator vessel receives $CO_2$ gas from the $CO_2$ tank through one or more conduits which connect the $CO_2$ tank with the inlet of the extractor-separator vessel, wherein the extractor-separator vessel includes an extraction chamber for housing organic material to be extracted, a collection zone located at the bottom portion of the extractor-separator vessel and a main body located between the extraction chamber and the collection zone, wherein $CO_2$ vapor enters the top portion of the extractor-separator vessel and is liquefied to a supercritical fluid, wherein the liquefied $CO_2$ is passed through the organic material housed within the extraction chamber to extract various compounds and is subsequently delivered to the collection zone, wherein the collection zone includes a filtration system which comprises a first series of filtration chambers, a second series of filtration chambers and a third series of filtration chambers, wherein each series of filtration chambers comprises a first chamber and a second chamber and a flow control/pressure relief valve to control the flow of liquid $CO_2$ between the first chamber and the second chamber within each series of filtration chambers, wherein each chamber houses a high pressure filter membrane and a pressure gauge positioned before and after the filter membrane within each chamber to indicate how much extract is filled within the chamber housing the filter membrane, wherein the extractor-separator vessel further comprises at least one conduit allowing the liquefied $CO_2$ exiting the filtration system to be recirculated through the extraction chamber after the liquefied $CO_2$ passes through at least one filtration chamber, wherein the high pressure filter membrane within the first series of chambers has a pore size greater than the high pressure filter membrane within the second series of chambers and wherein the high pressure filter membrane within the second series of chambers has a pore size greater than the high pressure filter membrane within the third series of chambers; and an accumulator comprising an inlet and an outlet, wherein the accumulator receives $CO_2$ from the extractor-separator pressure vessel through one or more conduits.

Also provided is a method of extracting compounds from an organic material. The method includes the following steps: providing the extraction system of claim 10; pressurizing $CO_2$ vapor as it enters the extractor-separator pressure vessel to form liquid $CO_2$; passing liquefied carbon dioxide through the organic material within the extraction chamber of the extractor-separator pressure vessel; delivering a $CO_2$ vapor/oil mixture at a pressure of about 800 psi and a temperature of about 120° F. to the collection zone; heating the collection zone to a temperature between about 85 to about 100° F.; heating the main body of the extractor-separator pressure vessel to about 100° F.; heating the condenser within the extractor-separator pressure vessel to between about 85 to about 100° F.; and collecting extracted and separated materials from the collection zone.

III. BRIEF DESCRIPTION OF THE DRAWINGS

IV. DETAILED DESCRIPTION

Figure 1:
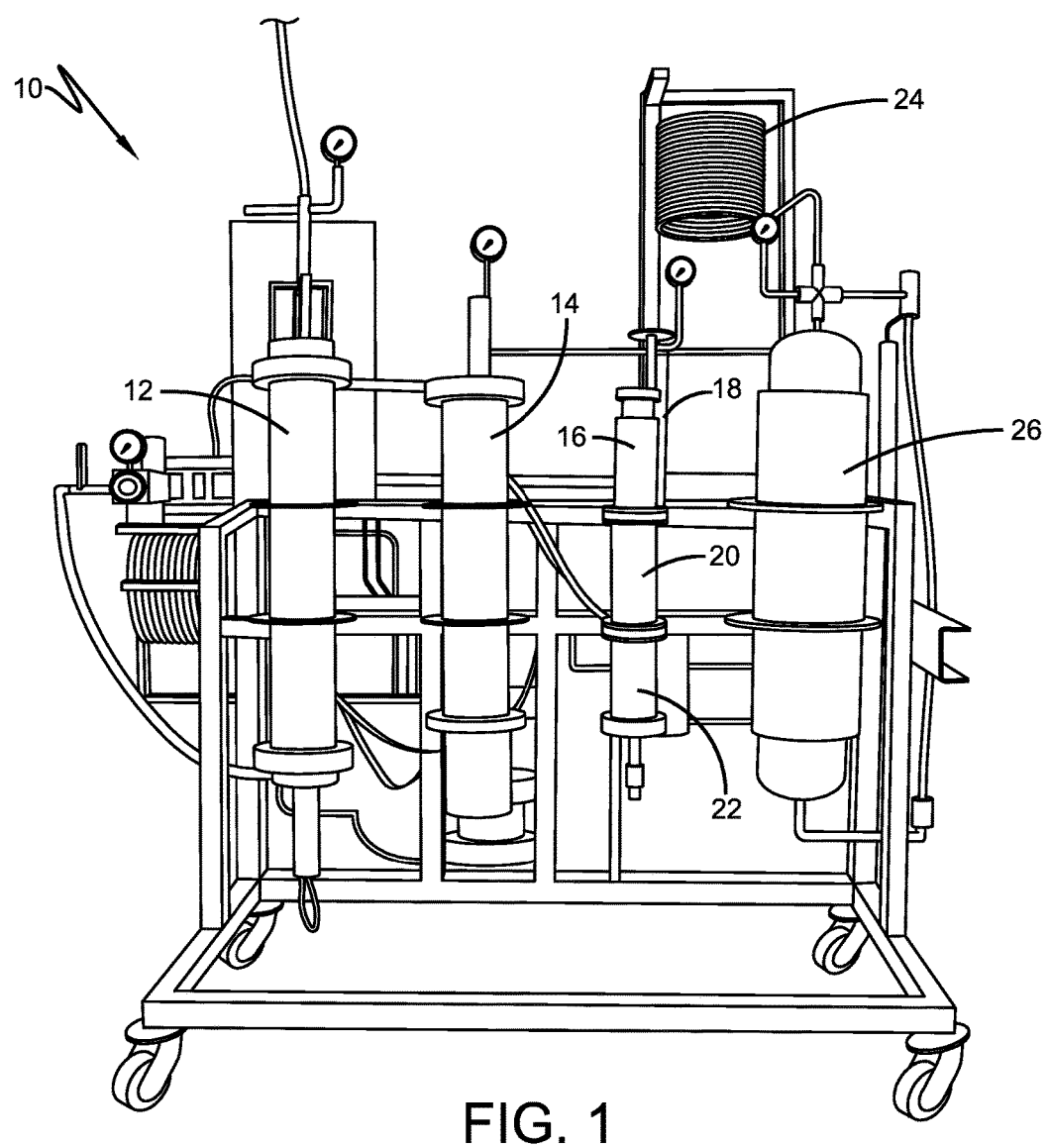
FIG. 1 illustrates an exemplary $CO_2$ extraction system.

Provided is an extraction system and associated methods which may optionally incorporate the use of a filtration system. The extraction system may incorporate the use of any type of extracting material or solvent for use within the system. In certain embodiments, the extraction system incorporates the use of $CO_2$ as the extracting material and may be referred to as a $CO_2$ extraction system. The $CO_2$ extraction system may include various component parts, including but not limited to a $CO_2$ source (e.g., a $CO_2$ tank), various pumps, an extractor or pressure vessel, optionally a filtration system, optionally at least one separator and a collection vessel. In certain embodiments, however, parts of the extraction system may operate without the use of a pump. The $CO_2$ extraction system may also optionally include a dual purpose apparatus, also referred to herein as an extractor-separator pressure vessel, which can be added to a supercritical $CO_2$ extraction system. In certain embodiments, the dual purpose apparatus may be used in combination with an integrated filtration system for isolating monoterpenes, light oils and other organic compounds. In other embodiments, the dual purpose apparatus may be used alone in combination with a non-integrated filtration system to perform a high pressure distillation/extraction with $CO_2$ or other compressed gasses.

As mentioned above, a typical $CO_2$ extraction system generally operates in the following manner. First, plant or other organic or raw materials are inserted into an extractor vessel (hereinafter referred to as the "extractor"). Next, $CO_2$ gas is pumped from the $CO_2$ tank through a conduit to the extractor. The extractor is pressurized and maintained at a certain temperature so that $CO_2$ gas is compressed to a liquid or supercritical fluid upon its entry into the extractor. The extractor may be pressurized anywhere from about 800 to about 15,000 pounds per square inch (psi) and the temperature of the extractor may be set anywhere from 20° C. to about 50° C. In certain cases the extractor is pressurized up to about 1000 psi. In certain embodiments, the exterior of the extractor is insulated with an insulation jacket to assist in maintaining the temperature within the extractor. The liquefied $CO_2$ passes through the plant or other organic or raw material within the extractor and acts as a solvent, removing (i.e., extracting) various oils and compounds from the plant or other raw materials. The liquefied $CO_2$ containing the extracted oils and compounds is then transferred or pumped to a separator. The separator is maintained at a different temperature and pressure than the extractor which results in the separation of the oil and other extracted compounds from the liquefied $CO_2$ and the conversion of liquefied $CO_2$ into $CO_2$ gas. In certain embodiments, the separator is maintained at a pressure ranging from about 200 psi to about 400 psi and may be maintained at a higher temperature than the extractor. For example, the temperature of the separator may be set from about 50° C. to about 60° C. The oil and other extracted compounds fall into a collection vessel at the bottom of the separator while the $CO_2$ gas is transferred or pumped through a conduit to either the $CO_2$ tank or to the extractor to be recirculated through the system.

In certain embodiments, the $CO_2$ extraction system may also include one or more additional separators which operates in a manner similar to the first separator described above. For example, the $CO_2$ extraction system may include a second separator which is designed to receive overflow liquid $CO_2$ from the first separator (i.e., liquid $CO_2$ which has not had time to convert to $CO_2$ gas) and/or liquefied $CO_2$ from the extraction vessel which is transferred or pumped simultaneously from the extraction vessel to both the first separator and the second separator.

The present disclosure provides several variations to this typical extraction system described above. These variations may, in certain embodiments, incorporate the use of a filtration system. The filtration system may be incorporated into the extraction system after the liquefied $CO_2$ passes through the plant or other organic or raw material within the extractor to remove or extract the various oils and compounds from the plant or other raw materials. In certain embodiments, the filtration system may be incorporated within the interior of the extraction vessel. In other embodiments, the filtration system may be a unit which is separate from the extraction vessel and which is positioned outside of and between the extraction vessel and the separator. In such embodiments, the filtration system may provide additional means for separating oil and other extracted compounds from the liquefied $CO_2$ in addition to the separator to obtain a greater yield of extraction. In further embodiments, the filtration system may be used in place of the separator vessels to obtain the extraction, thereby obviating the need for additional equipment such as vessels, pumps and valves and the need for additional energy output associated with pressurizing, de-pressurizing and maintaining specific temperature fluctuations to operate one or more separators downstream from the extractor. In one embodiment, the extraction system includes a filtration system outside of the extraction vessel and does not include a first separator or a second separator. In other embodiments, the filtration system may be incorporated within the interior of one or more separator vessels, outside of and between a first separator and second separator vessel or downstream from the separator vessels.

In certain embodiments, the filtration system includes at least one chamber with at least one filter membrane for retaining the desired extracted constituents. The filter membrane may, in certain embodiments, be a high pressure filter membrane. In certain embodiments, there is a series of chambers with filter membranes for retaining the desired extracted constituents. More particularly, in certain embodiments, the filtration system may include three series of chambers. The first series of chambers may include a chamber or group of chambers which has the largest pore openings for capturing the largest molecules. Such molecules are typically waxes and chlorophyll. The second series of chambers may include a chamber or group of chambers which are smaller and designed to capture the desired oils and resins containing valued constituents. The third series of chambers may include a chamber or group of chambers which have the smallest pore size and are for capturing monoterpenes or essential oils. It should be understood that present disclosure also encompasses the use of any number of chambers or series of chambers including more or less than three series of chambers as well as any number of chambers within each particular series and that in certain embodiments, the chambers may receive extracted constituents through the use of a pump, although a pump may not be required in other embodiments as the extracted constitutes may be gravity fed to the chambers. It should also be understood that the positioning of filter membranes is not limited to the order of those having the largest to those having the smallest pore openings and that present disclosure encompasses the positioning of filter membranes in any order.

In certain embodiments, each series or stage of filter membranes may include at least two chambers which alternate back and forth during operation through the use of a flow control/pressure relief valve. As one filter chamber becomes filled with extracted material, it will begin to clog. Pressure gauges may be positioned before and after the filter membrane (i.e., a gauge upstream from the filter chamber and a gauge downstream from the filter chamber) to indicate when clogging begins to occur. When the filter is clean, both the upstream and the downstream filter gauges will read the same pressure. As the membrane begins to fill with extract, a pressure differential will begin to manifest. Pressure begins to build upstream of the filter membrane and pressure begins to drop downstream from the filter membrane. This pressure differential will be noted on the upstream and downstream filter gauges. At a certain point, valving must be switched to direct the flow of extract saturated with $CO_2$ to the other, fresh filter chamber. When this occurs, the extract saturated chamber will be removed, cleaned and the extract harvested. The flow control/pressure relief valve between the chambers will allow the operator to readily switch flow from one chamber to another chamber containing at least one filter membrane. It will also allow the chambers to be de-pressurized prior to opening.

As the liquid $CO_2$ passes through the last chamber it may, in certain embodiments, flow back to the inlet of the pump and then flow back through the inlet of the extraction vessel where it will dissolve and extract more compounds in a continuous closed loop until extraction is complete. When the extraction is complete, there will no longer be a pressure differentiation between the pressure gauges on the upstream and downstream of the filter membranes. This is because upon completion of the extraction process, no extract would be building up and clogging the chambers. This design is particularly advantageous because the loss of pressure differences between the chambers provide the operator with an indication that the extraction process is complete. This is in contrast to current extraction system designs which provide no way of indicating the completion of the extraction process leaving it up to the experience and skill of the operator to know how long an extraction will take.

Upon completion of the extraction process, a valve and pump system may be used to switch or redirect flow of the $CO_2$ back to the storage containers for later use. Once the extractor is fully de-pressurized, the extractor is opened up and the spent solids are disposed of. The filters within the filtration system may also be removed and cleaned.

In certain embodiments, the extraction vessel of the present disclosure has a working pressure ranging from about 2,000 psi to about 15,000 psi. The extraction vessel can be fully opened at each end for cleaning and for placing material for extraction within the extractor. As explained above, in certain embodiments, the filtration system may be incorporated within the extraction vessel. In such embodiments, the extraction vessel of the present disclosure also includes at least one filter ranging from about 40 to about 100 microns at top and/or bottom of the extractor to prevent solid material from flowing out of the extractor. In certain embodiments, the extraction vessel may be jacketed for heating and cooling. Pressurization of the extraction vessel as described in the embodiments set forth herein may be generally achieved through a high pressure liquid pump having either an electric or a pneumatic drive.

The above disclosure sets forth basic information with respect to the operation of a $CO_2$ extraction system and a filtration system incorporated within a $CO_2$ extraction system. Variations of the above-described $CO_2$ extraction system, incorporated filtration system, and corresponding processes include the following embodiments.

In one embodiment of the $CO_2$ extraction system, the separation and collection steps occur within two or more pressurized vessel(s). For example, the separation and collection steps may occur within one or more separator vessels and/or an extractor-separator pressure vessel. The separator is considered a low pressure vessel relative to the extraction vessel. In one embodiment, plant or other raw materials are inserted into the extraction vessel, $CO_2$ gas is pumped from the $CO_2$ tank through a conduit into the extraction vessel, which is pressurized and maintained at a certain temperature to compress the $CO_2$ gas into a liquid or supercritical fluid. The liquefied $CO_2$ then passes through the plant or other raw material within the extraction vessel and acts as a solvent, removing (i.e., extracting) various oils and compounds from the plant or other raw materials. The liquefied $CO_2$ containing the extracted oils and organic compounds is then transferred to a separator. The separator is maintained at a different temperature and pressure than the extraction vessel which results in the separation of the oil and other extracted compounds from the liquefied $CO_2$ and the conversion of liquefied $CO_2$ into $CO_2$ gas. The separator is designed to separate heavier compounds from the liquefied $CO_2$. As these heavier compounds are separated from the liquefied $CO_2$, the liquefied $CO_2$ vaporizes and rises to the top portion of the separator. This vaporized $CO_2$ is entrained with remaining volatile oils and other organic compounds that have yet to be separated from the $CO_2$.

The vaporized $CO_2$ entrained with the remaining volatile oils and other organic compounds is then transferred to an extractor-separator pressure vessel (also referred to as a light oil separator) through conduit running between one or more separator vessels and the extractor-separator pressure vessel. In certain embodiments, however, the extraction system may include an extractor-separator pressure vessel which, compared to the separator, is used to separate lighter oils. The extractor-separator pressure vessel or light oil separator has three distinct zones: a condenser zone located at the top portion of the vessel, a collection zone at the bottom portion of the vessel, and a main body located between the condenser zone and the collection zone. In certain embodiments, the $CO_2$ vapor entrained with volatile oils and other organic compounds enters the top portion of the extractor-separator pressure vessel through a "bore through tube" or "dip tube" at approximately 800 psi and 120° F. which converts the $CO_2$ vapor back to a supercritical fluid or liquid. The dip tube then delivers the liquefied $CO_2$/oil mixture to the bottom of the vessel where the collection zone is located. The collection zone (first zone) is maintained at a temperature ranging from about 85° F. to about 100° F. and at a pressure which allows the supercritical $CO_2$ fluid to vaporize. As the supercritical $CO_2$ fluid vaporizes, it separates itself from the oils contained in the fluid and begins to rise within the main body portion (second zone) of the extractor-separator pressure vessel which is maintained at a temperature ranging from about 100° F. to about 120° F. and at a pressure which allows the supercritical $CO_2$ to remain vaporized. The oils that were entrained within the supercritical $CO_2$ fluid separate from the liquefied $CO_2$ at the bottom portion of the extractor-separator pressure vessel and enter the collection zone for collection by the end user.

As the vaporized $CO_2$ rises through the second zone, it enters the condenser zone (third zone) of the extractor-separator pressure vessel. The vaporized $CO_2$ next contacts a condenser (also referred to as a coldfinger condenser) maintained at a temperature ranging from about 85° F. to about 100° F. within the third zone of the extractor-separator pressure vessel. At this point, any oils remaining within the $CO_2$ vapor that did not condense in the bottom of the vessel condense out on the coldfinger condenser, drip onto and pass through the material that is being extracted for further extraction and drip back to the collection zone at the bottom of the vessel for collection by the end user. The vaporized $CO_2$ then passes through the coldfinger condenser and runs out of the extractor-separator pressure vessel to be reclaimed within another vessel designated as the accumulator or is disposed. In certain embodiments, as the vaporized $CO_2$ exits the extractor-separator pressure vessel and enters the accumulator, it may be re-liquefied for further use within the extraction system. In such embodiments, the re-liquefaction of $CO_2$ gas occurs within a second condenser which is external to the extractor-separator pressure vessel. It is understood that $CO_2$ gas is transferred between the extractor-separator pressure vessel, second condenser and accumulator through various conduits, valves, pressurized valves, pumps as would be deemed necessary by a person of ordinary skill in the art. It is also noted that coldfinger condenser includes two condenser ports which function as an inlet and outlet for fluid passing through the condenser. Further details with respect to the extractor-separator vessel are provided throughout this disclosure.

In summary, when incorporated into the extraction system, the extractor-separator pressure vessel may include three zones for pressurizing, heating and cooling $CO_2$ gas as it passes through the extractor-separator pressure vessel. These zones include a condenser, a main body and a collection zone. In certain embodiments, the condenser is located at the top portion of the extractor-separator pressure vessel and in some embodiments is positioned on the bottom portion of the lid of the extractor-separator pressure vessel. The collection zone is located at the bottom portion of the extractor-separator pressure vessel and the main body is located between the condenser and the collection zone. Each of these zones is maintained at a certain temperature and pressure depending on the state of the extraction process. The extraction process of this first embodiment begins with $CO_2$ gas entering the pressure vessel through a bore through port at the top portion of the extractor-separator pressure vessel where it is pressurized to form a supercritical $CO_2$ fluid or $CO_2$ liquid. In certain embodiments, $CO_2$ gas is exposed to a pressure of 1000 psi at this point in the extraction process. The $CO_2$ gas is now incorporated into the plumbing stream within the extractor-separator pressure vessel. The compressed or liquid $CO_2$ passes through the extractor-separator pressure vessel where it contacts the plant or other organic or raw material that has been placed within the extractor-separator pressure vessel. The liquid $CO_2$ acts as a solvent extracting or picking up the compounds from the plant or other raw material. As such, the extractor-separator pressure vessel may be referred to as a $CO_2$ extractor. It is noted that the plant or other organic or raw material is ground up prior to insertion into the pressure vessel in order to enhance the extraction process. In certain embodiments, the plant or other raw material is ground up into a fine-grained collection of materials.

The present disclosure also provides for the incorporation of a filtration system within this first variation of a basic $CO_2$ extraction system. As described above, in embodiments wherein the extraction system includes a separate extraction vessel and one or more separator vessels in combination with the separate extraction vessel, the filtration system may be incorporated either within the extraction vessel, outside of and between the extraction vessel and a separator vessel, within a separator vessel or outside of and between one or more separator vessels (e.g., outside of and between a first separator and a second separator). The filtration system may provide additional means for separating oil and other extracted compounds from the liquefied $CO_2$ in addition to the separator and extractor-separator pressure vessel to obtain a greater yield of extraction. In further embodiments, the filtration system may be incorporated within the extractor-separator pressure vessel. In such embodiments, the filtration system may be positioned below the extraction chamber and above the collection zone of the extractor-separator pressure vessel. In further embodiments, the filtration system may be a separate unit which is positioned downstream from the extractor-separator pressure vessel. In such embodiments, the filtration system may be positioned after a second condenser which is external to and downstream from the extractor-separator so as to accept re-liquefied $CO_2$. The re-liquefied $CO_2$ may then enter the accumulator for storage and further use and recirculation within the extraction system.

It is noted that the above described apparatus and method which incorporates the use of the extractor-separator pressure vessel further allows any moisture that is present within the system to condense out at the coldfinger condenser. Water is the enemy of $CO_2$ extraction as it changes the polarity and pH of the $CO_2$, disrupting the efficiency of the extraction process.

Thus, the $CO_2$ extraction system in the embodiment described above includes an extraction vessel and optionally at least one separator in combination with the extraction vessel positioned within the plumbing stream between the tank and the accumulator. It is understood to a person of ordinary skill in the art that the $CO_2$ extraction system embodiments described above may include various valves, pumps and other mechanical features as necessary to allow for the passage of supercritical $CO_2$ throughout the system, although the need for such components may be reduced in certain embodiments. It is also understood that a person of ordinary skill could readily determine the temperatures and pressures which allow for the conversion of $CO_2$ gas to a supercritical fluid and vice versa, although the need for such pressure and temperature fluctuations may be reduced in certain embodiments.

In another embodiment of the $CO_2$ extraction system, the extraction, separation and collection steps occur in a single pressurized vessel (i.e., within an extractor-separator pressure vessel). In this type of extraction system, the extraction system may omit the use of the extraction vessel and/or a separator pressure vessel in combination with an extraction vessel. In such embodiments, the extractor-separator pressure vessel may receive liquid $CO_2$ directly from the extraction vessel or may receive $CO_2$ gas directly from a tank containing $CO_2$ gas. As mentioned above, the extractor-separator pressure vessel has three distinct zones: a condenser zone located at the top portion of the vessel, a collection zone at the bottom portion of the vessel, and a main body located between the condenser zone and the collection zone. The extraction process begins with plant or other organic or raw material being placed within an extraction chamber within the extractor-separator pressure vessel. The extraction chamber may, in certain embodiments, include a basket for holding the material to be extracted. In certain embodiments, the basket is a stainless steel basket. In further embodiments, the basket is perforated. In yet further embodiments, the basket is a perforated stainless steel basket. In yet further embodiments, the basket is a perforated stainless steel basket which is lined with a cloth or paper filter. The plant or other organic or raw material is thoroughly dried, ground up and placed within the basket. The basket is then placed within the bottom of the vessel and positioned underneath a coldfinger condenser which is incorporated within the bottom portion of the lid of the extractor-separator pressure vessel. In certain embodiments, the basket is referred to as a Soxhlet Basket.

Next, $CO_2$ vapor enters the extractor-separator pressure vessel through a "bore through tube" or "dip tube" and is liquefied as a result of the temperature and pressure settings of the extractor separator. The dip tube then delivers the liquefied $CO_2$ to the extraction chamber positioned towards the bottom portion of the vessel where the basket containing the plant, or other organic or raw material is located. In an alternative embodiment, liquid $CO_2$ is injected through a center port that goes from the outside of the vessel, though the center of the coldfinger condenser (positioned on the bottom portion of the lid) and into the interior of the vessel. In a further alternative embodiment, $CO_2$ can be introduced within the extractor-separator pressure vessel by placing dry ice within the vessel along with the basket. The dry ice would then liquefy based on the pressure and temperature settings of the vessel. Other gases and solvents can also be introduced using this method.

The liquefied $CO_2$ then flows through the main body of the extractor-separator vessel and enters the basket, saturating the plant or other organic or raw material and acting as a solvent, extracting oils and other compounds (e.g., monoterpenes) from the plant or other organic or raw material. In certain embodiments, the basket is positioned near the bottom portion of the extractor-separator pressure vessel near the collection zone (first zone). After the plant or other organic or raw material is saturated with liquid $CO_2$, the collection zone or bottom of the extractor may be heated to approximately 120° F. The main body (second zone) of the extractor-separator pressure vessel may be maintained at a temperature of about 75° F. and the condenser (third zone) may be cooled to between about 50 to about 75° F. These heating and cooling parameters initiate a distillation cycle in which vapor will liquefy on the condenser and drip through the basket of plant or other organic or raw materials. The liquid $CO_2$ will extract specific constituents (e.g., oil, monoterpenes or other compounds) out of the plant or other organic or raw material and deposit them within the collection zone at the bottom of the extractor-separator pressure vessel. The heat within the collection zone at the bottom of the extractor-separator pressure vessel will then vaporize the $CO_2$ or solvent and leave the extract behind. As the liquid $CO_2$ vaporizes, it travels through the main body zone to the condenser zone (third zone) of the extractor-separator pressure vessel. When the vaporized gas contacts the condenser, it re-liquefies forming droplets on the condenser. These droplets of liquefied $CO_2$ then drip down onto the plant or other organic or raw material within the basket to repeat the same extraction and separation process described above.

In order to terminate the recirculation process, the temperature of the condenser may be increased to a certain temperature known to a person of ordinary skill in the art which would allow the vaporized $CO_2$ to remain in gas state and to exit the extractor-separator pressure vessel. In certain embodiments, the vaporized $CO_2$, exits the extractor-separator pressure vessel through a condenser port where it travels to an external condenser to be re-liquefied before it is transferred to an accumulator for storage and re-use.

This collection zone (first zone) is located at the bottom portion of the vessel and may be maintained at a temperature between about 85 to about 100° F. and at a pressure which allows the supercritical $CO_2$ fluid to vaporize. As the supercritical $CO_2$ fluid to vaporizes, it separates itself from the oils contained in the fluid and begins to rise within the main body portion (second zone) of the second separator which may be maintained at a temperature ranging from about 100 to about 120° F. The oils that were entrained within the supercritical $CO_2$ fluid separate from the liquefied $CO_2$ and enter the collection zone for collection by the end user. Thus, the second variation of the $CO_2$ extraction system described above encompasses a single combined extractor-separator pressure vessel positioned upstream from the second external condenser and the accumulator.

The present disclosure also provides for the incorporation of the filtration system described above within this second variation of a basic $CO_2$ extraction system. The filtration system may be incorporated into the extraction system after the liquefied $CO_2$ passes through the plant or other organic or raw material within the extractor-separator pressure vessel to remove or extract the various oils and compounds from the plant or other raw materials. In such embodiments, the filtration system may be incorporated within the extractor-separator pressure vessel itself to remove or extract the various oils and compounds from the plant or other raw materials before the liquefied $CO_2$ vaporizes or be a separate unit positioned between the extractor-separator pressure vessel and the accumulator. In such embodiments, the filtration system may provide additional means for separating oil and other extracted compounds from the liquefied $CO_2$ in addition to the separator component of the extractor-separator pressure vessel to obtain a greater yield of extraction. In one embodiment, the filtration system may be positioned below the extraction chamber and above the collection zone of the extractor-separator pressure vessel to allow for further extraction of the desired compounds from the liquefied $CO_2$. In another embodiment, the filtration system described above may be a separate unit which is positioned outside of and downstream from the extractor-separator pressure vessel. In such embodiments, the filtration system may be positioned after the second condenser referenced above which is external to the extractor-separator pressure vessel so as to accept re-liquefied $CO_2$ from the second external condenser. After the re-liquefied $CO_2$ passes through the filtration system, the re-liquefied $CO_2$ may then enter the accumulator for storage and further use within the extraction system.

In a further variation of the extraction system, the extractor-separator pressure vessel used in any of the embodiments disclosed herein may include a filtration system as described herein in place of a coldfinger condenser to separate oils and other organic compounds including but not limited to monoterpenes.

Also provided is a method of extracting compounds from an organic material involving the use of any of the extraction systems described herein. The method generally includes the following steps although it is apparent to a person of ordinary skill in the art that various modifications to the steps will vary depending upon the specific components utilized within the extraction system based on the present disclosure: 1) providing a $CO_2$ extraction system; 2) providing an extracting material such as $CO_2$ gas and pressurizing the $CO_2$ gas to form a supercritical liquid; 3) passing the supercritical liquid through an organic material within an extraction vessel or a vessel which is partly designed for extraction; 4) separating organic material from the supercritical liquid by at least one of the following steps—passing the supercritical liquid through at least one separator vessel, passing the supercritical liquid through a vessel which is partly designed for separation of organic material from the supercritical liquid or by passing the supercritical liquid through a filtration system; 5) collecting extracted and separated materials from a separator vessel or a vessel which is partly designed for separation of organic material from the supercritical liquid; 6) storing and recirculating the extracting material through the extraction system.

It is understood to a person of ordinary skill in the art that the $CO_2$ extraction system described above may include various valves, pumps and other mechanical features as necessary to allow for the passage of fluid (including liquids and gasses) throughout the system. It is further understood to a person of ordinary skill in the art that the $CO_2$ tank, extraction vessel, first separator, the extractor-separator pressure vessel, accumulator, filtration system and other component parts include various inlets and outlets as necessary to allow fluids to pass between the various vessels and component parts connected within the extraction system. It is also understood that a person of ordinary skill could readily determine the temperatures and pressures which allow for the conversion of $CO_2$ gas to a supercritical fluid and vice versa.

Figure 2:
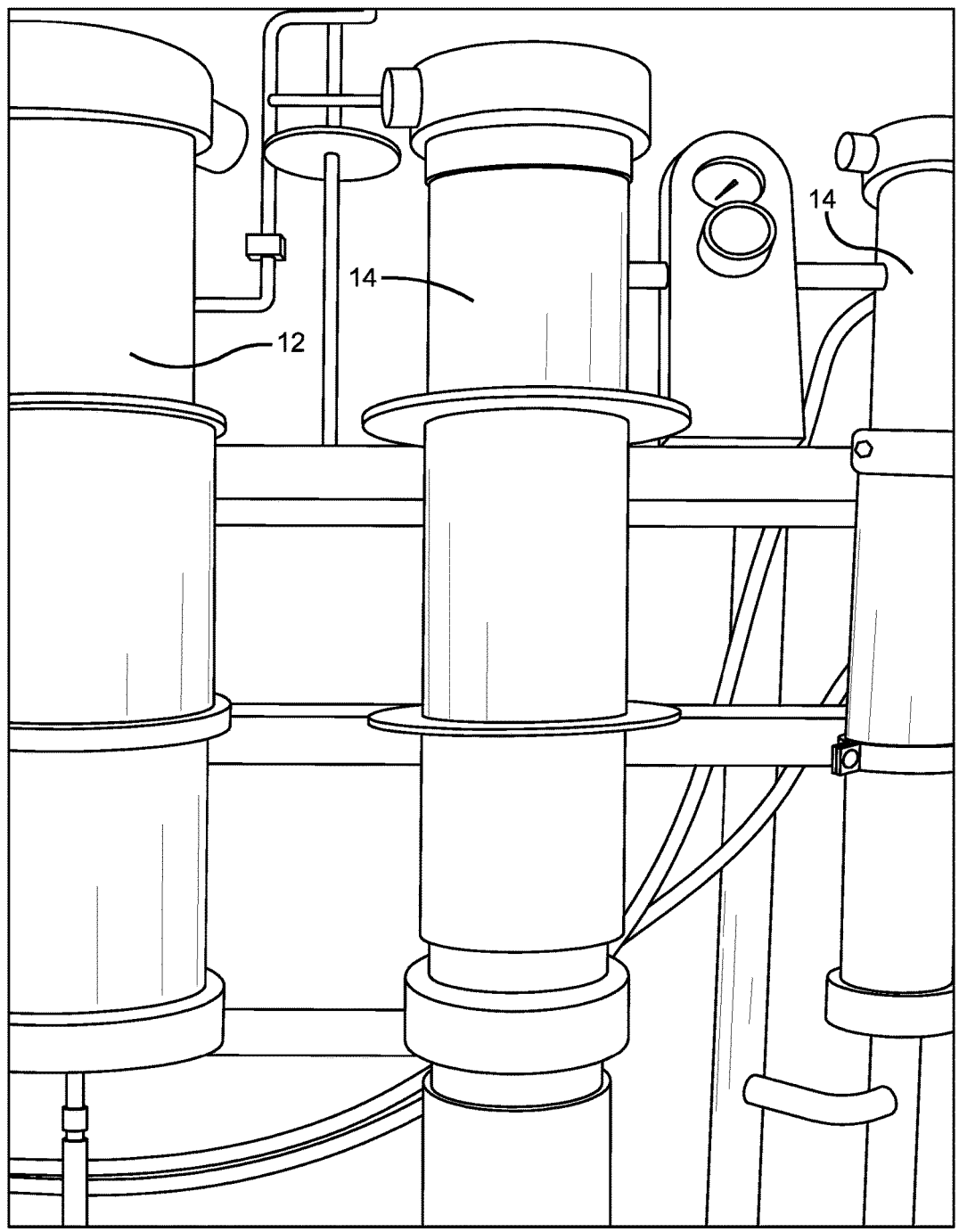
FIG. 2 illustrates an exemplary extraction vessel and separator of an exemplary $CO_2$ extraction system.
Figure 3:
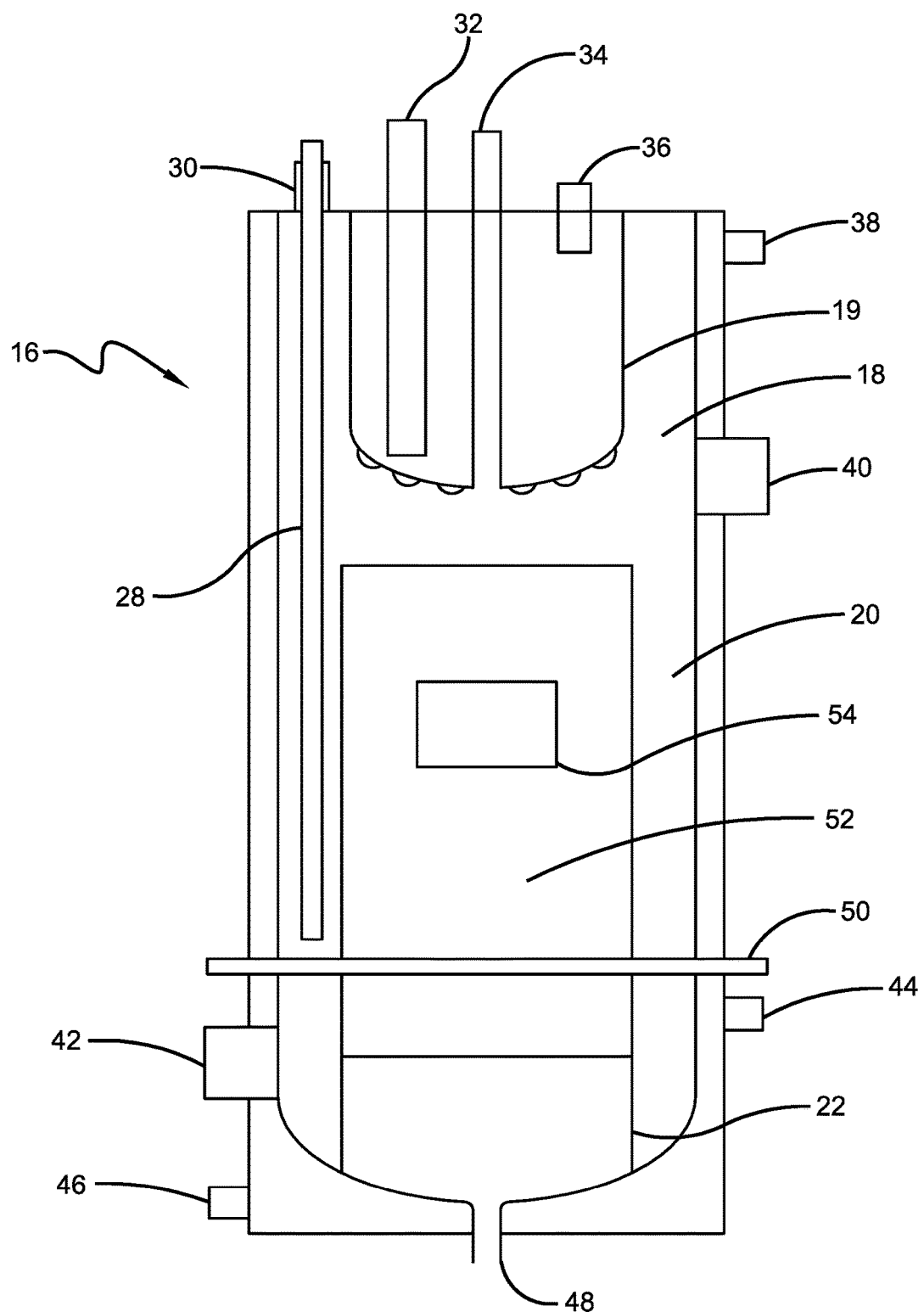
FIG. 3 illustrates an exemplary extractor-separator pressure vessel of an exemplary $CO_2$ extraction system.
Figure 4:
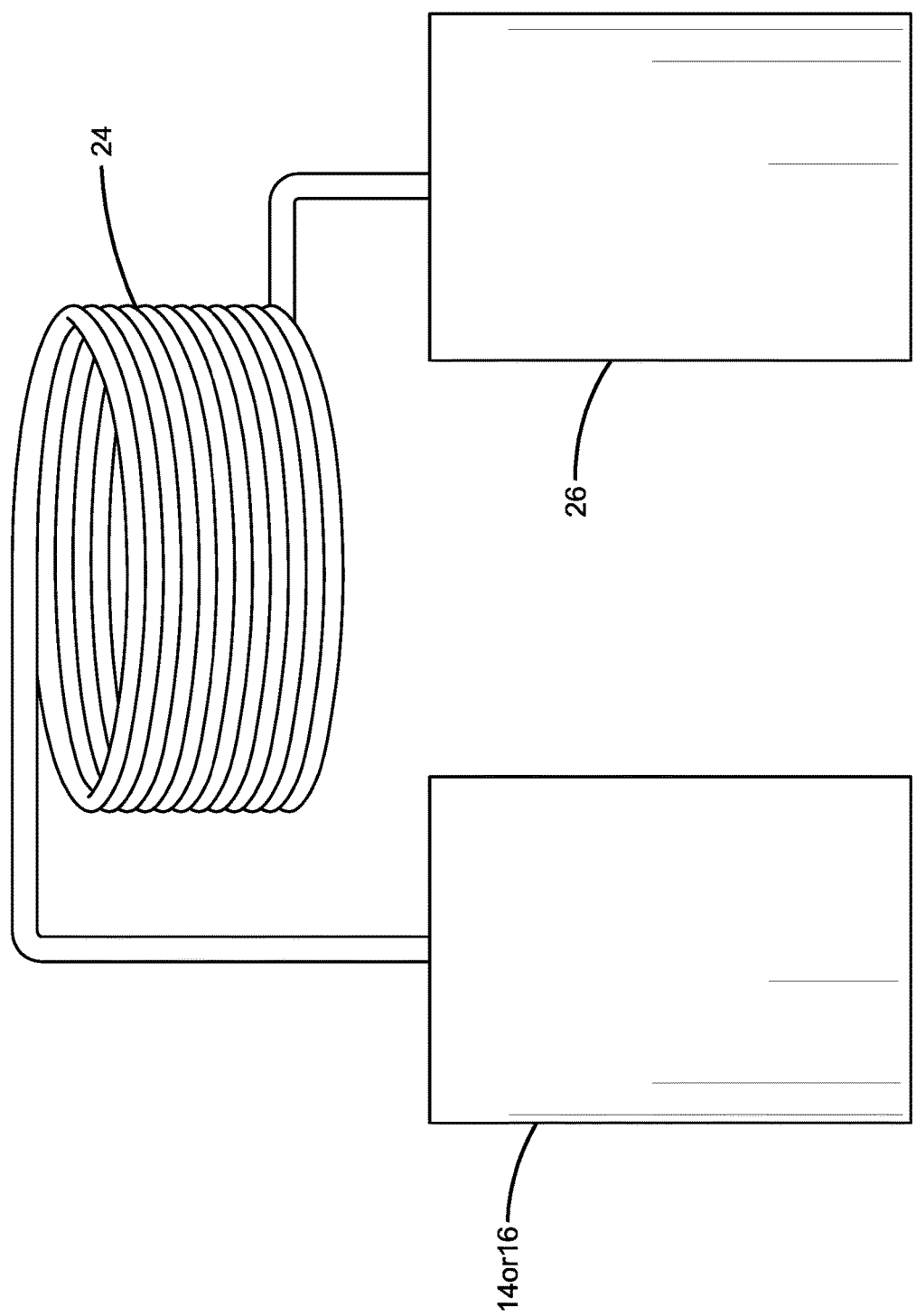
FIG. 4 is a diagram illustrating the positioning of an external condenser between a separator or an extractor-separator pressure vessel and an accumulator within an exemplary $CO_2$ extraction system.
Figure 5:
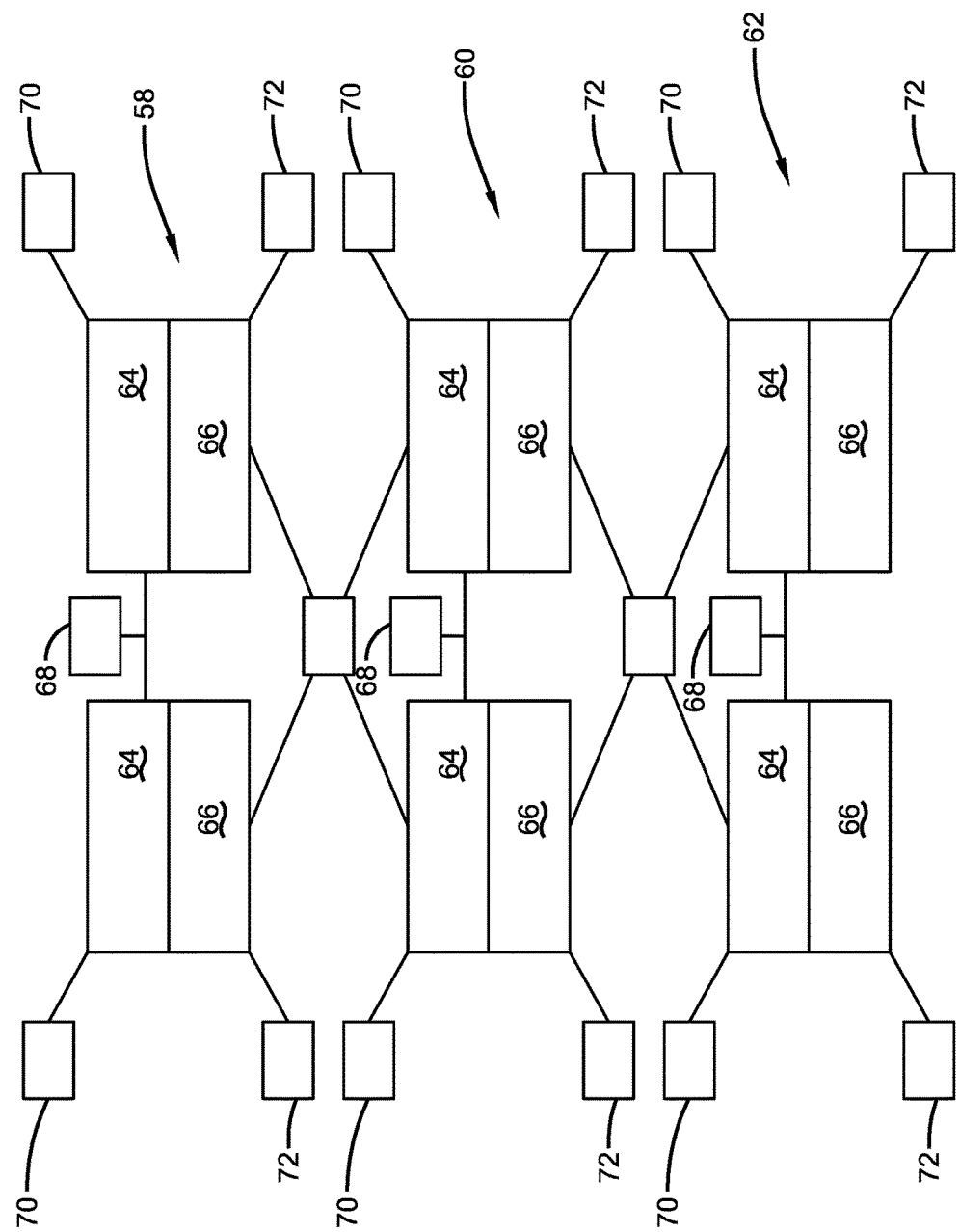
FIG. 5 is a diagram illustrating the component parts of an exemplary filtration system.
Figure 6:
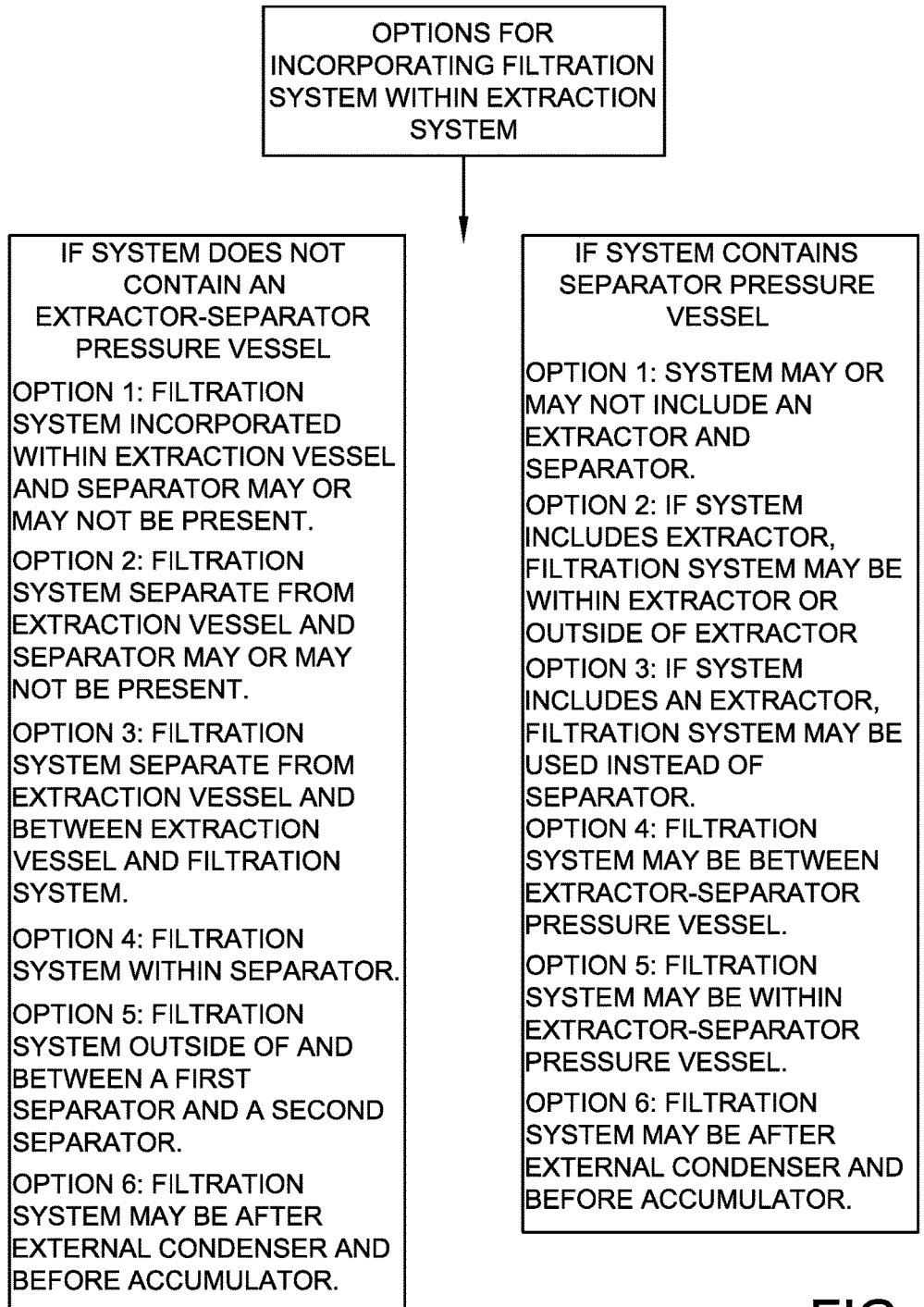
FIG. 6 is a chart which lists various options for incorporating the filtration system within an extraction system.

Illustrations of various embodiments of this disclosure are provided within FIGS. 1 through 6. FIG. 1 illustrates an exemplary $CO_2$ extraction system (10) which includes an extraction vessel (12), a separator (14), an extractor-separator pressure vessel (16), an external condenser (24) and an accumulator (26). The extractor-separator pressure vessel includes a condensation zone (18), a main body (20) and a collection zone (22). FIG. 2 illustrates an insulated extraction vessel (12) and a first and second separator (14) within a $CO_2$ extraction system. FIG. 3 illustrates the various component parts of an exemplary extractor-separator pressure vessel (16) which includes a bore through port (30) for receiving $CO_2$ gas, a bore through tube (28) for passing supercritical $CO_2$ fluid to an extraction chamber (52) which houses the organic material to be extracted within a soxhlet basket (54). As the supercritical fluid passes through the organic material, the extracted mixture enters the collection zone (22) which is heated to evaporate the supercritical fluid in order to separate the extracted constitutes from the supercritical fluid. The separated extracted materials are collected through a collection tube (48). $CO_2$ vapor then rises from the collection zone (22) through the main body (20) to the condensation zone (18) and condenses on a coldfinger condenser (19). The coldfinger condenser (19) includes two condenser ports (32) and (36) which allow fluid to enter and exit the condenser (19) to maintain a relatively cold temperature. As the condensation forms on the coldfinger condenser (19), it begins to drip through the extraction chamber (52) and the Soxhlet basket (54) containing the organic material to be extracted. This results in further extraction of the organic material as the supercritical fluid renters the collection zone (22) where the liquid $CO_2$ is once again evaporated in order to separate the extracted material from the supercritical $CO_2$ fluid. This evaporation-condensation cycle repeats until the organic material is fully extracted. To stop the evaporation-condensation cycle, the temperature of the coldfinger condenser (24) is adjusted to stop the formation of liquid $CO_2$ on the surface of the coldfinger condenser (24). $CO_2$ vapor continues to rise through the center tube (34) to exit the extractor-separator pressure vessel (16) to be re-liquefied in an external condenser (24) and ultimately stored in an accumulator (26) for re-use within the extraction system as shown within FIG. 4. It is noted that FIG. 3 illustrates various view ports (42) and (44) located respectively at the collection zone and the condensation zone which allows the end user to view and observe the extraction process. In addition, FIG. 3 also illustrates heating/cooling jacket ports at the condensation zone (38) and at the collection zone (42) and (44) which are used to transfer fluid within the extractor-separator pressure vessel to maintain the temperature specifications of the system. FIG. 5 is a diagram which illustrates an exemplary filtration system (56) which may be present at various points within the extraction system. The filtration system (56) includes a first series of filter chambers (58), a second series of filter chambers (60) and a third series of filter chambers (62). Each series of filter chambers includes two filter chambers (64) and each filter chamber (64) includes a filter membrane (66). The filter membrane (66) may have various pore sizes between each series of filter chambers. Pressure within each filter chamber is monitored by an upstream pressure gauge (70) and a downstream pressure gauge (72). When the pressure differential between these two gauges indicate that a particular chamber is full, a flow control valve is used to redirect flow of the supercritical fluid containing extract to the second filter chamber (64) within the series. As the supercritical fluid is filtered within each series of filter chambers, it passes to the next series for further filtration of progressively smaller compounds. FIG. 6 is a chart which lists the various options for incorporating the filtration system within the extraction system disclosed herein. A table of the reference numbers found within the drawings is provided below.

| Table of Reference Numerals within the Drawings |
|---|
| 10 - Extraction System |
| 12 - Extraction Vessel |
| 14 - Separator |
| 16 - Extractor-Separator Pressure Vessel |
| 18 - Condensation Zone |
| 20 - Main Body |
| 22 - Collection Zone |
| 24 - External Condenser |
| 26 - Accumulator |
| 28 - Bore Through Tube |
| 30 - Bore Through Port |
| 32 - Condenser Port |
| 34 - Center Tube |
| 36 - Condenser Port |
| 38 - Heating/Cooling Jacket Port |
| 40 - Condenser View Port |
| 42 - Collection Zone View Port |
| 44 - Heating/Cooling Jacket Port |
| 46 - Heating/Cooling Jacket Port |
| 48 - Collection Tube |
| 50 - Flange |
| 52 - Extraction Chamber |
| 54 - Soxhlet Basket |
| 56 - Filtration System |
| 58 - First Series of Filter Chambers |
| 60 - Second Series of Filter Chambers |
| 62 - Third Series of Filter Chambers |
| 64 - Filter Chamber |
| 66 - Filter Membrane |
| 68 - Flow Control Valve |
| 70 - Upstream Pressure Gauge |
| 72 - Downstream Pressure Gauge |

While the $CO_2$ extraction system has been described above in connection with various illustrative embodiments, it is to be understood that other similar embodiments may be used or modifications and additions may be made to the described embodiments for performing the same function disclosed herein without deviating therefrom. Further, all embodiments disclosed are not necessarily in the alternative, as various embodiments may be combined or subtracted to provide the desired characteristics. Variations can be made by one having ordinary skill in the art without departing from the spirit and scope hereof. Therefore, the soilless growth medium should not be limited to any single embodiment, but rather construed in breadth and scope in accordance with the recitations of the appended claims. The right to claim elements and/or sub-combinations that are disclosed herein as other inventions in other patent documents is hereby unconditionally reserved.

Having thus described the disclosed system and method, it is now claimed:

1. An extraction system comprising:
   a tank containing $CO_2$ gas which comprises an inlet for filling the tank with $CO_2$ gas and an outlet for allowing the gas to be transferred within the extraction system;
   an extractor-separator pressure vessel comprising a top portion, a bottom portion, an inlet and an outlet wherein the extractor-separator pressure vessel receives $CO_2$ gas from the $CO_2$ tank through one or more conduits which connect the $CO_2$ tank with the inlet of the extractor-separator pressure vessel, wherein the extractor-separator pressure vessel includes an extraction chamber positioned towards the bottom portion of the extractor-separator pressure vessel for housing organic material to be extracted, a condenser zone located at the top portion of the extractor-separator pressure vessel, a collection zone located at the bottom portion of the extractor-separator pressure vessel and a main body located between the condenser zone and the collection zone, wherein the collection zone, main body and condenser zone are continuous with each other and integrally formed within the extractor-separator pressure vessel, wherein $CO_2$ vapor enters the top portion of the extractor-separator pressure vessel through a bore through port and bore through tube and is pressurized to form a supercritical fluid, wherein the supercritical $CO_2$ is passed through the organic material housed within the extraction chamber to extract various compounds and is subsequently delivered to the collection zone, wherein the collection zone is maintained at a temperature and a pressure which allows the supercritical $CO_2$ fluid to vaporize and separate itself from oils contained in the supercritical $CO_2$ fluid, wherein the vaporized $CO_2$ rises within a main body portion of the extractor-separator pressure vessel separating itself from compounds entrained within the supercritical $CO_2$, wherein the vaporized $CO_2$ enters the condenser zone of the extractor-separator pressure vessel and contacts a condenser maintained at the top portion of the extractor-separator pressure vessel, wherein any organic compounds remaining within the $CO_2$ vapor condenses out on the condenser and drips to the extraction chamber to further extract compounds from the organic material and subsequently enters the collection zone at the bottom portion of the extractor-separator pressure vessel for collection, wherein the condenser comprises two condenser ports and a center tube, wherein the two condenser ports allow fluid to enter and exit the condenser to maintain an operating temperature for extraction and to adjust the operating temperature for terminating extraction, wherein the center tube which allows $CO_2$ vapor to exit the extractor-separator pressure vessel upon termination of the extraction, wherein the continuous and integrated arrangement of the collection zone, main body and condenser zone within the extractor-separator pressure vessel allow for continuous extraction without having to stop the extraction process.

2. The extraction system of claim 1, further comprising a filtration system which is integrated within the extraction system in at least one of the following arrangements—1) outside of and upstream from the extractor-separator pressure vessel; 2) within the extractor-separator pressure vessel; and 3) outside of and downstream from the extractor-separator pressure vessel.

3. The extraction system of claim 2, wherein the filtration system is integrated within the extractor-separator pressure vessel.

4. The extraction system of claim 3, wherein the organic material is housed within a stainless steel perforated basket within the extraction chamber, further wherein the basket is lined with a filter.

5. The extraction system of claim 3, wherein the filtration system is positioned below the extraction chamber, further wherein the filtration system comprises a first series of filtration chambers, a second series of filtration chambers and a third series of filtration chambers, wherein each series of filtration chambers comprises a first chamber and a second chamber and a flow control/pressure relief valve to control the flow of supercritical $CO_2$ between the first chamber and the second chamber within each series of filtration chambers, wherein each chamber houses a high pressure filter membrane and a pressure gauge positioned before and after the filter membrane within each chamber to indicate how much extract is filled within the chamber housing the filter membrane, wherein the extractor-separator pressure vessel further comprises at least one conduit allowing the supercritical $CO_2$ exiting the filtration system to be recirculated through the extraction chamber after the supercritical $CO_2$ passes through at least one filtration chamber, wherein the high pressure filter membrane within the first series of chambers has a pore size greater than the high pressure filter membrane within the second series of chambers and wherein the high pressure filter membrane within the second series of chambers has a pore size greater than the high pressure filter membrane within the third series of chambers.

6. The extraction system of claim 1 wherein the extracted compounds include oil and monoterpenes.

7. A method of extracting compounds from an organic material comprising the following steps:
   providing the extraction system of claim 1;
   pressurizing $CO_2$ vapor as the $CO_2$ vapor enters the extractor-separator pressure vessel to form supercritical $CO_2$;
   passing supercritical carbon dioxide through the organic material within the extraction chamber of the extractor-separator pressure vessel;
   delivering a $CO_2$ vapor/oil mixture at a pressure of about 800 psi and a temperature of about 120° F. to the collection zone;
   heating the collection zone to a temperature between about 85 to about 100° F.;
   heating the main body of the extractor-separator pressure vessel to about 100° F.;
   heating the condenser within the extractor-separator pressure vessel to between about 85 to about 100° F.; and
   collecting extracted and separated materials from the collection zone.

* * * * *